(12) United States Patent
Fortune et al.

(10) Patent No.: US 9,383,310 B2
(45) Date of Patent: *Jul. 5, 2016

(54) APPARATUS AND METHOD FOR INSPECTING AN ARTICLE

(71) Applicant: ROLLS-ROYCE PLC, London (GB)

(72) Inventors: James Robert Fortune, Derby (GB); Alison Joanne Heath, Derby (GB); Sebastien Parent, Montreal (CA)

(73) Assignee: ROLLS-ROYCE plc, London (GB)

( * ) Notice: Subject to any disclaimer, the term of this patent is extended or adjusted under 35 U.S.C. 154(b) by 37 days.

This patent is subject to a terminal disclaimer.

(21) Appl. No.: 14/472,924

(22) Filed: Aug. 29, 2014

(65) Prior Publication Data

US 2015/0070687 A1 Mar. 12, 2015

(30) Foreign Application Priority Data

Sep. 6, 2013 (GB) .................................. 1315912.4

(51) Int. Cl.
*G01N 21/00* (2006.01)
*G01N 21/55* (2014.01)
*G01N 23/00* (2006.01)

(52) U.S. Cl.
CPC ................ *G01N 21/55* (2013.01); *G01N 23/00* (2013.01)

(58) Field of Classification Search
CPC ....... G01N 21/55; G01N 21/64; G01N 21/68; G01N 23/00; G01N 2015/1037; G01J 3/02; H01J 37/32935
USPC ...................................... 356/72–73, 300–445
See application file for complete search history.

(56) References Cited

U.S. PATENT DOCUMENTS

| 4,747,684 A | 5/1988 | Weiser |
| 2002/0005952 A1 | 1/2002 | Sugai et al. |
| 2010/0103256 A1 | 4/2010 | Rauber |
| 2015/0070689 A1* | 3/2015 | Fortune .................. G01N 21/95 356/138 |

FOREIGN PATENT DOCUMENTS

| DE | 197 25 535 A1 | 12/1998 |
| EP | 2 161 566 A1 | 3/2010 |
| GB | 2288961 A | 11/1995 |

(Continued)

OTHER PUBLICATIONS

Jan. 27, 2015 Search Report issued in European Application No. 14 18 2637.

(Continued)

*Primary Examiner* — Abdullahi Nur
(74) *Attorney, Agent, or Firm* — Oliff PLC (57) ABSTRACT

A method of determining the orientation of a grain structure of a turbine blade or vane using an optical technique, illuminates a surface with a beam from a light source and then manipulates the relative orientation of the surface, a light beam and detector to determine the relative orientation which provides the peak reflectance of the beam from the surface to the detector. Further surfaces of the component are similarly manipulated and illuminated and the orientation of the grain structure calculated from the determined relative peak reflectance orientations of the surface, first further surface and second further surface. Determination of the grain orientation allows the value of high angle boundaries to be determined. Also disclosed is apparatus suitable for performing the method.

11 Claims, 5 Drawing Sheets

(56) References Cited

FOREIGN PATENT DOCUMENTS

| | | |
|---|---|---|
| JP | A-4-249749 | 9/1992 |
| WO | WO 99/22224 A1 | 5/1999 |
| WO | WO 01/46992 A2 | 6/2001 |
| WO | WO 2013/150424 A1 | 10/2013 |

OTHER PUBLICATIONS

Search Report issued in British Patent Application No. 1315912.4 dated Feb. 20, 2014.

* cited by examiner

APPARATUS AND METHOD FOR INSPECTING AN ARTICLE

TECHNICAL FIELD OF INVENTION

The present invention relates to methods for examining an article and in particular apparatus for detecting artefacts that present on the surface of the article and particularly where the article is formed of a single crystal alloy.

BACKGROUND OF INVENTION

High value articles often require inspection to determine their condition and to identify whether there are any defects.

The invention seeks to provide an improved apparatus and method to detect or identify defects or surface artefacts that are presented on the surface of an article.

STATEMENTS OF INVENTION

According to an aspect of the invention there is provided a method of determining the value of a boundary between the primary grain and the secondary grain in a component, the method comprising the steps of: identifying a boundary between a primary grain and a secondary grain which are presented on a surface of the component; illuminating the primary grain with a beam from a light source and manipulating the relative orientation of the surface, beam and a detector detecting the light reflected from the surface and determining a first relative orientation which provides the peak reflectance of the beam to the detector; illuminating the secondary grain with a beam from a light source and manipulating the relative orientation of the surface, beam and a detector detecting the light reflected from the surface and determining a second relative orientation which provides the peak reflectance of the beam to the detector; and comparing the difference between the first and second relative orientations.

Preferably the step of comparing the difference gives a value that indicates the magnitude of the angle boundary. The value may be compared to a threshold range having high, low and medium tolerance ranges, the component being sentenced depending on the band in which the value corresponds. The component may be scrapped when the value corresponds to the high tolerance range, passed as fit for service when the value corresponds to the low tolerance range, or passed for further analysis when the value corresponds to the medium tolerance range.

The further analysis may inspect the surface with an x-ray to determine the value of the boundary.

The step of manipulating the surface may include adjusting the roll, pitch and/or yaw of the surface.

The roll, pitch and yaw may be adjusted by moving the surface in a first ellipse or circle about a pivot point. Reflectance values may be taken at a plurality of locations as the surface is moved in the circle or ellipse about the pivot point. The surface may moved in a further ellipse or circle of different size to the first ellipse or circle.

The relative orientation may be an average of the relative orientations giving a reflectance value that is within 10 percent of an absolute peak reflectance.

The orientation of a grain structure in a component may be determined by a method comprising; presenting a surface of the component to a detector and illuminating the surface with a beam from a light source; manipulating the relative orientation of the surface, beam and detector and determining the relative orientation which provides the peak reflectance of the beam from the surface to the detector; presenting a first further surface of the component to the detector and illuminating the first further surface with a beam from a light source; manipulating the relative orientation of the first further surface, beam and recording device and determining the relative orientation which provides the peak reflectance of the beam from the surface to the detector; presenting a second further surface of the component to the detector and illuminating the second further surface with a beam from a light source; manipulating the relative orientation of the second further surface, beam and detector and determining the relative orientation which provides the peak reflectance of the beam from the surface to the detector; calculating the orientation of the grain structure from the determined relative peak reflectance orientations of the surface, first further surface and second further surface.

Preferably the surface is manipulated by adjusting its roll, pitch and/or yaw relative to an incidence angle of the beam. The component may be mounted onto a support that permits the blade orientation or article orientation to be adjusted. The position of the peak reflectance may be an averaged position taken from the orientation of the surface, first further surface or second further surface where a spot peak reflectance is within 90% of the maximum spot peak reflectance.

Preferably at least the pitch and yaw of the surface are manipulated simultaneously.

Preferably the pitch and yaw are manipulated simultaneously by pivoting the component about an axis in a circular or elliptical movement. A detector may be used to capture the peak reflectance at a number of spaced positions as the component is pivoted through the circle or ellipse. The movement through each circle or ellipse may not be along the entire periphery of the circle or ellipse and the transfer between circles or ellipses may be continuous such that the component pivots in a spiral. Preferably the spaced positions are equally spaced. The size of the circle or ellipse may be subsequently changed and the detector used to capture further reflectance values.

The light source may be one of a plurality of separately electable light sources, the relative orientation being manipulated by electing a first one of the light sources to provide the beam and switching to a second elected light source to provide the beam.

Each light source is preferably a Light Emitting Diode (LED). The light source may be mounted to a translatable fixture, the fixture being movable from a first location to a second location.

The peak reflectance may be determined from the maximum averaged detected reflectance value of the surface.

Preferably the component is a gas turbine component with a primary grain. The grain may have a cubic face centred crystal lattice.

Preferably the component is a blade or vane. The primary grain is preferably oriented along the stress axis of the blade of vane. The blade may have a root and an aerofoil and the surface is the underside of the blade root.

The optical orientation of the grain structure may be determined in an apparatus for determining a surface characteristic of an article, the apparatus comprising a detector for detecting the surface characteristic of the article; and an illumination support adapted to provide a plurality of nominal light locations each of which is separately electable and from which a beam of light may be directed to the article.

Each of the nominal light locations may be adapted to direct the beam of light to a common focal point.

Preferably the illumination support comprises a concave surface having the plurality of nominal light locations.

The concave surface may be a dome, each nominal light location comprising an aperture adapted to receive an electable light source. The aperture is preferably sized to receive a pen light that can be inserted and removed therefrom. The dome may be a spherical cap or faceted to approximate a spherical cap. The facets with the apertures may be arranged to orientate a beam generated by the light source to a common focal point. Each nominal light location may comprise an electable light source. The electable light sources may be secured to a mat that is provided to the concave surface of the dome. Advantageously, each light source can be tested before the mat is secured to the concave surface.

Preferably the nominal light locations are arranged as a plurality of concentric circles. Each nominal light locations in each of the concentric circles may be regularly spaced.

The concave surface may be an arm, each nominal light location comprising an electable light source. The arm may have a mount that is moveable along the arm to a plurality of predetermined positions corresponding to the nominal light locations, wherein the mount carries an electable light source.

The arm may have a proximal end and a distal end and the arm can pivot about the proximal end.

Preferably each electable light source in the above arrangements is a Light Emitting Diode (LED). Each LED may be focussed to the same focal point.

The detector may be a camera. The camera may be able to capture still or moving pictures. The detector is preferable mounted at the proximal end of the arm or at the crown of the dome, which is the location through which, if an axis extends, there is symmetry in the dome.

The apparatus may further comprise a component mount for locating a component in a predetermined location relative to the nominal light locations.

The component mount may be adapted to adjust one or more of the roll, pitch or yaw of a component mounted therein relative to the nominal light locations.

With the primary grain identified, possibly using the above methods and apparatus, it is possible to determine the presence of an artefact presented on a surface of a component having a primary grain crystal orientation, the method possibly comprising the steps of: illuminating the surface at a relative orientation between a light source, a detector and the primary grain crystal orientation which provides a peak reflectance to the detector; and translating the surface to inspect for a change in reflectance detected by the detector.

Preferably the change in reflectance is a discontinuity having an abrupt change in reflectance. The surface may be translated by adjusting one or more of the roll, pitch or yaw of the surface.

The peak reflectance may be detected and averaged for a region of interest (ROI) on the surface. The region of interest may be the whole surface or a subset thereof.

Preferably the detector captures an image and the image is transferred to a processor that records the value of the detected reflectance.

Preferably the recorded values are compared and a difference between two or more detected values that are greater than a threshold difference indicates the presence of an artefact.

A method may further comprise the step of presenting the component to an illumination support adapted to provide a plurality of nominal light locations each of which is separately electable and from which a beam of light may be directed to the article and electing a first light location that provides peak reflectance of the primary grain to the detector. The surface may then be translated and a further light location elected that is different from the first light location the further light location being selected to provide peak reflectance of the primary grain to the detector.

Preferably the step of electing a first or further light location includes the step of providing a beam of light from a light source at the first or further light location to a region of interest on the surface (ROI).

The method may further comprise the step of presenting a further surface of the component to the detector, illuminating the further surface at a relative orientation between a light source, the detector and the primary grain crystal orientation which provides a peak reflectance to the detector; and translating the surface to inspect for a change in reflectance detected by the detector.

The change in reflectance from the surface and the change in reflectance from the further surface may be compared for a periodic response for determining the presence of a secondary grain.

The invention will now be described by way of example only and with reference to the accompanying drawings, in which:

DETAILED DESCRIPTION OF INVENTION

Figure 1:
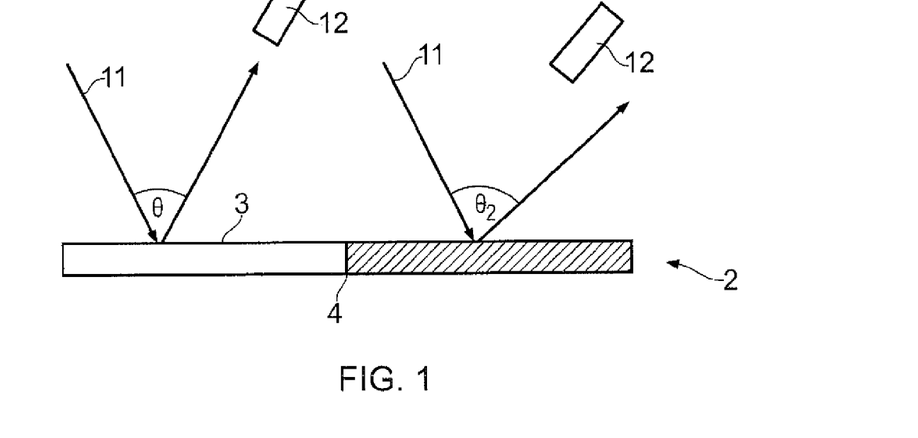
FIG. 1 depicts a schematic of a single crystal component having a crystal boundary.

FIG. 1 depicts an article 2 such as a single crystal turbine blade. In some articles more than one grain can grow and can extend in different directions to the primary grain; these grains are called secondary grains. Each grain has a grain boundary and the difference can be inspected optically where they are presented at the surface of the component. Such a boundary, where the difference or magnitude in the angle between primary and secondary growth axis is high, can be relatively easy to visibly detect due to a large change in contrast between primary and secondary but it is more difficult to detect where the difference in the grain angle between each of the portions is low. High Angle Boundaries (HAB) are artefacts that are indicative of an article that is flawed and unsuitable for use in the aggressive, high temperature environments of a gas turbine. Articles that have HAB are usually scrapped.

The axis of the primary grain in a turbine blade is preferably oriented, within limits, along the stacking axis of the blade which is an axis running the length of the blade from the root to the tip. Therefore, whilst some deviation from the true axis of the blade is permissible the deviation should not be greater than a predetermined threshold value. It is difficult to determine the value of the angle boundary in both manual and automatic inspection processes and it is often necessary to inspect using X-ray or other expensive and potentially harmful methods.

Different grain angles reflect incident light in different directions. Therefore, the primary grain, secondary grains and high angle boundaries may be detected using an optical technique where the grains are presented to an exterior face of the component.

This is depicted in FIG. 1 where a light beam is incident on the surface 3 of a component having a primary grain and a secondary grain (shown by the hatched portion) both of which present to the surface. When the beam is incident on the surface at an angle θ, the angle of reflectance can vary depending on the axis of the grain presented to the surface at the point of incidence and the angle of the surface 3 to the incident angle. Thus, the surface 3 in FIG. 1 is oriented so that the beam reflected from the primary grain on the left of the figure is directed to a recording device which can capture the reflectance value and/or an image of the surface. This is at peak reflectance and the primary grain is said to be in "bright field". Where the beam is incident to a secondary grain as shown by the hatched portion to the right of the figure the beam is incident on the surface at the same angle θ but is reflected from the surface at a different angle $θ'_2$ to that caused by reflectance from the primary grain. The captured image will be darker than the image captured from the primary grain.

A secondary grain presented to the surface is any grain that does not reflect light in the same way as the primary grain.

The maximum reflectance value is recorded where the incident beam is reflected from the surface directly into the recording device as shown in the left hand side of FIG. 1. For the right hand section of FIG. 1 a reflectance value is still captured by the camera but the value is lower as the maximum reflectance is directed past the camera. Advantageously, the primary, or the secondary grain, can be oriented such that it reflects in bright field i.e. at maximum reflectance and any opposing secondary or primary grain will be identified by an area that is darker and not reflecting in bright field.

Every beam incident on the surface of the component has six degrees of freedom that represent the three dimensional angle of incidence of the beam onto the surface (x, y, z) and the roll, pitch and yaw of the surface relative to the beam.

In a single crystal alloy turbine blade the primary grain is preferably oriented generally along an axis of the blade extending between the root and tip and within acceptable limits. Typically the crystal axis is substantially parallel with the blade stress axis which sets the orientation of one of the faces of the crystal grain but the orientation of the other crystal faces are not controlled in the manufacturing process which means that for blades with the same exterior profile the reflected light may be different and thus absolute values cannot easily be used.

Figure 2:
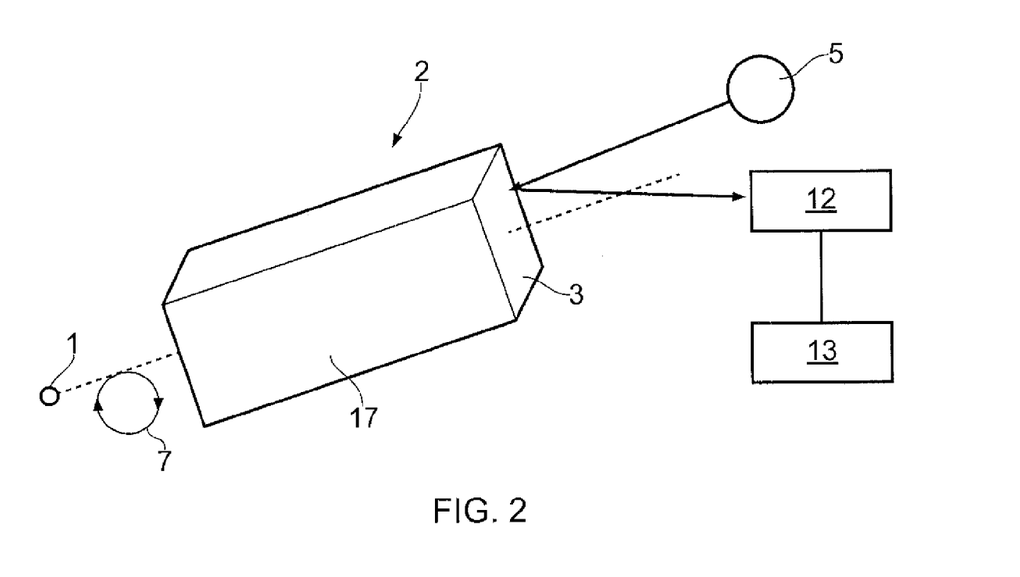
FIG. 2 is a schematic drawing showing apparatus for determining a primary grain.

If the primary grain is found it is possible to illuminate it in bright field which will allow secondary grains and defects to be observed as dark. To determine the primary grain angle apparatus as shown in FIG. 2 may be used. The article 2 is placed in a fixture with the surface 3 facing a recording device 12. The surface 3 represents the root of a blade, where the article is a blade used in a turboengine, and is illuminated from a light source 5 that directs a beam onto the surface and which is reflected by the surface to the camera. The camera captures the light intensity and records it as a numerical value in a processor 13.

The maximum reflectance will be captured in the recording device where the reflected beam is fully incident onto the recording device sensor. To determine whether the captured reflectance value is at a maximum it is necessary to record values at a number of incident angles determined by the x, y, z angles of the incidence of the beam to the surface and the local pitch, yaw and roll of the component at the point of incidence for a number of locations on the surface.

For a turbine blade where the crystal axis is preferably aligned within specified tolerances to the longitudinal axis of the blade the component is aligned with the root of the aerofoil, or one surface 3, facing towards the recording device 12. An axis that extends through the article is fixed at an origin 1 and is pivoted in an ellipse or circle around the origin and intensity values of the captured reflected light recorded at a number of uniformly spaced angles as the axis traverses through the ellipse or circle 7. This process conveniently captures a number of reflectance values at a number of locations and varies the x, y and z components of the incident angle and the roll, pitch and yaw of the component.

The size of the ellipse or circle can be varied in a manner which will adjust the roll, pitch and yaw of the surface presented to the beam. The position of the light source may also be adjusted to vary the x, y, z component. In practice a first spiral is made with the light in a fixed orientation and the results analysed for a peak. The spiral size is increased and the position of the light varied if it is determined appropriate by the processing apparatus. The circle size and/or the light position is varied until a maximum reflectance value is identified and the x, y, z, roll, pitch and yaw determined.

Advantageously, course, fine or superfine routines may be selected in which the pitch change and angular rotation before capture of a subsequent image can be chosen for speed, accuracy or a medium. For the course routine the pitch may vary in 5 degree intervals to a maximum acceptable range that is typically between 20 and 30 degrees from the nominal tilt set at zero, the angular rotation before image capture is preferably around 10 to 40 degrees. For the fine routine the pitch may vary in 2 degree intervals to a maximum acceptable range that is typically between 6 and 8 degrees from the nominal tilt set at zero, the angular rotation before image capture is preferably around 10 to 30 degrees. For the superfine routine the pitch may vary in 0.5 degree intervals to a maximum acceptable range that is typically between 2 and 3 degrees from the nominal tilt set at zero, the angular rotation before image capture is preferably around 10 to 40 degrees.

By using the same region of interest (ROI) for every picture taken the highest average intensity can be determined and this can be considered to be caused by reflectance from the primary grain.

In some circumstances, particularly where the primary grain is not aligned within the required tolerances a peak or maximum reflectance value will not found. In this case it can be quickly and easily confirmed that the aerofoil does not meet the required quality and can be scrapped.

An alternative process, rather than circling the surface first varies the pitch and captures values for this variable and then varies the yaw and captures values for this variable.

It is important to note that the exact value of the peak reflectance is not important since the grain angle is determined from the position giving the peak reflectance. Secondary factors, such as the quality of the polishing or etching of the surface will affect the recorded value of the reflectance.

The accuracy to the position of the peak at which the maximum reflectance value is determined depends on the change in size between the circle size and/or the change in position of the lighting (assuming the sensor of the recording device is in a fixed position and orientation) to the component.

Closer gradations, however, take more time to collect and require more processing time. An alternative to using the same gradations over the whole surface is to monitor for signs of a peak using relatively coarse gradations and once signs i.e. greater reflectance values returned from a particular selection of x, y, z, roll, yaw and pitch are observed the closer gradations may be focussed around this peak.

This is advantageous as it is necessary to capture less data however, in practice, the momentum of the blade may mean that it is quicker and easier to traverse the axis continuously around the circumference of the circle and simply sample the data in the selected region.

Once sufficient data is captured it is possible to use the position of the light source, the position of the camera, the angle of the axis and the peak reflectance value and its position around the circumference of circle 7 to define the plane of the grain crystal face in space and determine the primary grain angle relative to the plane of the face 3.

In rare circumstances the blade is cycled and no peak is found i.e. the maximum reflectance value continues to increase. Typically this is because the determining process will measure the reflectance values up to the threshold point beyond which the difference of the primary grain axis to the blade axis is deemed to be unacceptable. Accordingly, it is not always necessary to find maximum reflectance value to determine whether a blade has an unacceptable grain angle.

Although the maximum reflectance value is likely to have been caused by the primary grain it is possible that another artefact, or secondary grain, may be the cause of the highest value. It is also important to note that where the maximum reflectance value is caused by a grain the value only captures one face and the orientation of the remaining faces has not been determined. It is therefore necessary to confirm that the maximum reflectance value is provided by a grain orientation and determine the axis of the grain in the component. The component, or aerofoil, is rotated about an axis orthogonal to the plane of the grain crystal face determined by inspection of the face 3 from which the maximum reflectance value has previously been determined to present a further surface to the incident beam and camera. For a single crystal nickel alloy the grain lattice is cubic so a rotation of 90 degrees is required. Alloys with different grain lattice angles should be rotated through an appropriate angle which may be different to 90 degrees.

The further face is then rotated about the axis 19 through the full 360 degrees. As each face is presented to the light source the grain at the surface will reflect the light and as the face rotates the intensity recorded by the camera will increase to a maximum where the face, grain, light and camera move into alignment and then decrease as the face, grain, light and camera move out of alignment.

If the maximum reflectance on face 3 is caused by a grain the periodic response from the component as it revolves about axis 19 will be cyclical which, for a cubic grain, will have equally spaced peaks at 90 degrees to each other owing to the cubic nature of the grain of the nickel alloys. Different shaped grains will generate a different response but it will still be periodic in nature as the grain moves in and out of alignment.

Where a defect or secondary grain is present the periodic response will be different and will either not be cyclical if the maximum reflectance on the face 3 is not generated by a grain boundary or will have unexpected peaks or troughs if a localised defect is present. More than one cyclical peak for a given face could be indicative of a secondary grain presented to the face.

Following this initial confirmation that the maximum reflectance from the first face 3 is due to a grain it is necessary to determine the orientation of the grain crystal face presented to the further face. This is achieved by following a similar approach to that for face 3. To determine the maximum reflectance, the face 19 is rotated about a pivot as described with regard to face 3. Because the structure of the grain is assumed to be cubic the sampling of the reflectance values can be prioritised to more limited set of face and light angles in order to speed up the measurement of the blade.

Once sufficient data is captured it is possible to use the position of the light source, the position of the camera, the angle of the axis and the peak reflectance value and its position around the circumference of circle 7 to define the plane of the crystal face in space and determine the primary grain angle relative to the plane of the face 19.

Absolute values are again not important because the reflectance value is affected by the surface finish of the blade. Aerofoils are also curved to provide an aerodynamic flow and the curvature of the blade relative to the crystal face can cause significant differences.

The component is then oriented orthogonally again to present a further face to the camera and the peak reflectance determined using the process described above to capture sufficient data to define the plane of the crystal face in space and determine the primary grain angle relative to the plane of this further face.

With all three crystal faces known it is possible to orientate the grain axis relative to the stacking axis of the component or aerofoil to determine whether it is within acceptable bounds.

Once the primary grain axis is established, it is known how to optimally illuminate the primary grain in every image. Since this optimal illumination returns a maximum reflectance value any deviation will be indicative of a defect or secondary grain.

To fully inspect the surface for a secondary grain a face is optimally illuminated to return the maximum reflectance for the primary grain. An image of the face is taken and examined using image processing software to determine whether there is a boundary between a region where the value of maximum reflectance is returned and a region where a value of less than maximum reflectance is returned. For the presence of a secondary grain the boundary will be straight.

If a boundary is detected its position on the blade can be determined through image recognition software. The presence of a secondary grain does not necessarily require the aerofoil to be scrapped. High grain angle boundaries (HAB) can give rise to unacceptable weakness in the component and it is necessary to calculate the difference in grain angles between the primary and secondary grains. Previously it has not been possible to calculate the value of the difference in grain angles using an optical method and it is typically achieved through an x-ray process which is both expensive and time consuming.

To determine the difference in value between the primary grain and a secondary grain the orientation of the primary grain is determined using x-ray or a process and apparatus similar to that described above. A region of the secondary grain is then inspected in a method similar to that described above with respect to the primary grain and the secondary grain orientation determined.

With both grain orientations now known the difference can be determined and where the difference is above a certain value then the component may be scrapped or further inspected using a conventional, usually time intensive, process such as x-ray inspection. Where the difference is less than the predetermined value the part is passed as being suitable for use.

Figure 3:
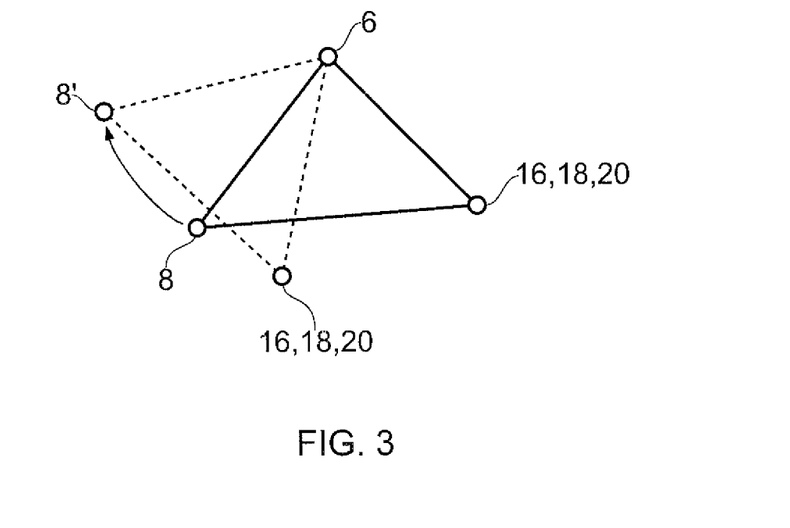
FIG. 3 depicts the relative angular positions of a detector, article and light source.

It has been found to be desirable that the part be examined under a known orientation between the article surface, the light and the detector. This is represented graphically in FIG.

3 where the camera 6 is arranged relative to both the part 8 and the light source 16, 18, 20. As the part surface is translated either rotationally or spatially relative to the camera either the position of the light source and/or the camera must also translate to maintain the same spatial angular arrangement between the light, article and detector. In FIG. 3 the camera is fixed and the light and the article are translated relative to it. By rotating the part through a number of different angles it is possible to identify significant light intensity changes that are indicative of a grain angle boundary. The greater the difference in grain angles at the boundary the more intense the difference in reflected light determined at the detector where one of the grains is aligned to reflect the maximum light onto the detector.

Figure 4:
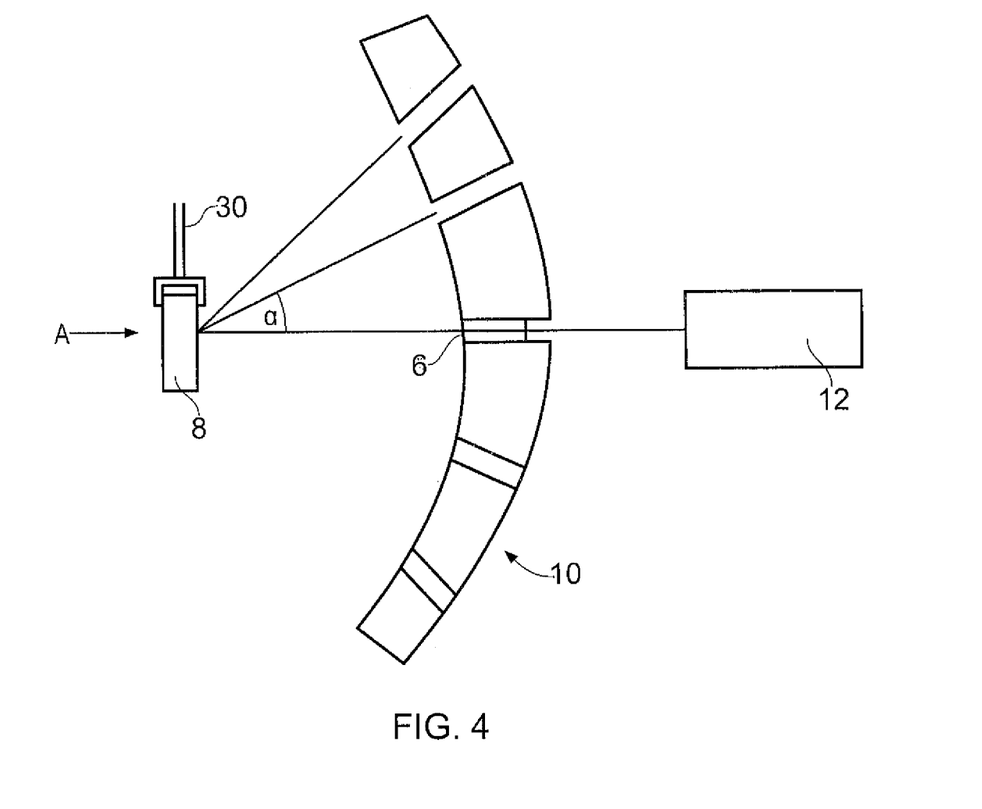
FIG. 4 depicts a first embodiment of an apparatus for detecting a high angle boundary.
Figure 5:
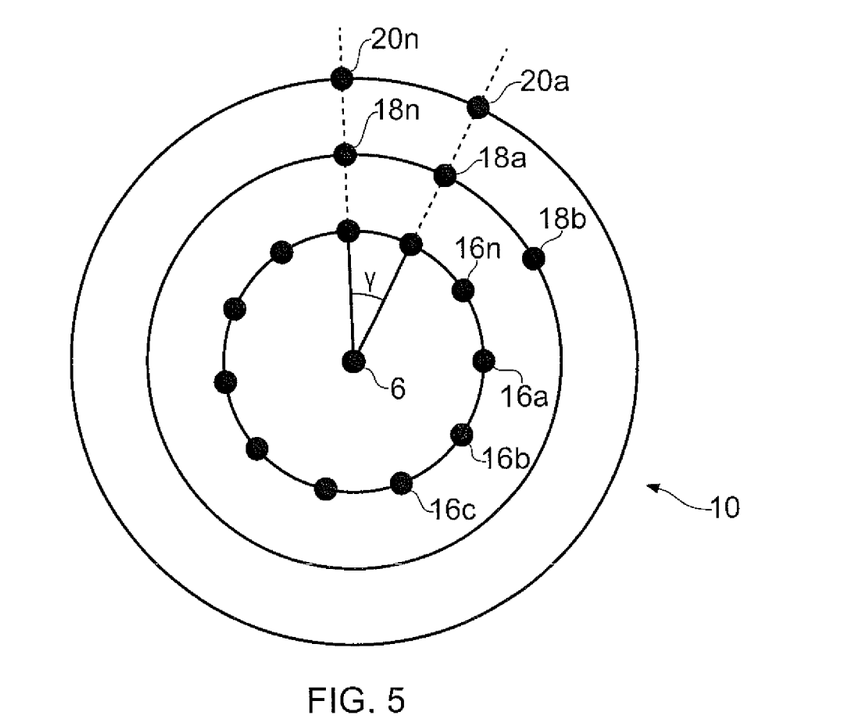
FIG. 5 is a view along arrow A of the apparatus of FIG. 2

In a first embodiment of the detection apparatus which is depicted in FIG. 4 the position of the detector 6 is fixed. The detection apparatus has a convex illumination support 10 within which is mounted a camera, or other suitable detection apparatus, which is focussed on the surface of the article 8 which is to be examined. The camera is connected to a processor 12 which acquires the image of the surface of the article, the light source used to generate the image, and the location and orientation of the article 8 and processes the image. The illumination support 10 has a plurality of apertures arranged in a series of concentric arrays 16, 18, 20. Each array has a constant angular pitch such that the apertures 16a, 16b, 16c . . . 16n; 18a, 18b, 18c . . . 18n; 20a, 20b, 20c . . . 20n are also aligned radially as shown in FIG. 5. The angle γ between each of the nominal light locations in the array 16a . . . 16n is calculated as 360/n or, in this particular embodiment, where n=11 about 32.7 degrees. The value of n is selected to provide the desired resolution of nominal light locations but is preferably between 10 and 72 per circular array; which gives an angle γ of between 2 and 36 degrees. Three or four circular arrays of nominal light locations are typically used, though in some circumstances a single array may suffice, which give a total number of nominal light locations of between 10 and 288.

Where larger numbers of nominal light locations are provided it is desirable to provide indicator on the surface of the support 10 that identify the nominal light locations.

Figure 6:
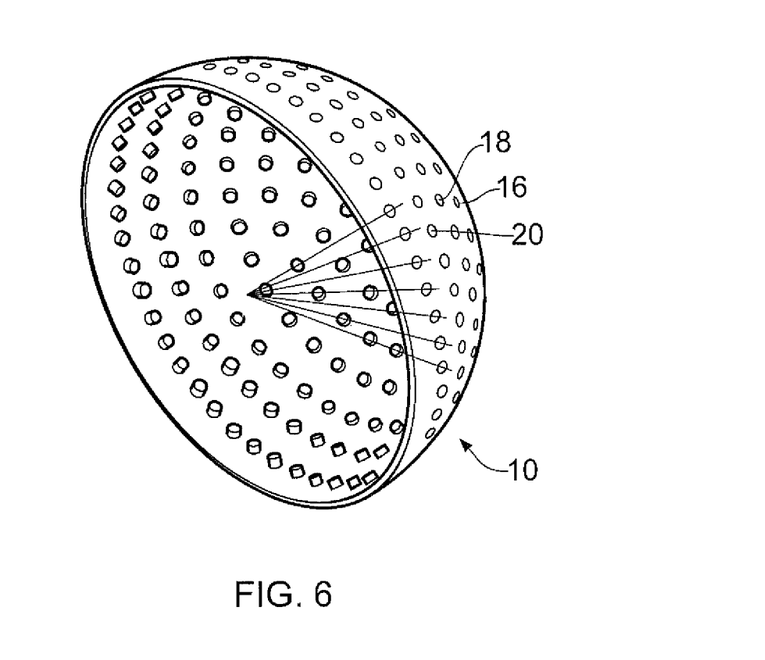
FIG. 6 is a perspective view of the apparatus of FIG. 2.

Each aperture extends through the illumination support 10 from the concave surface through to the convex surface at an angle which intersects the surface of the article at the focal point of the camera. Accordingly, each concentric array of apertures is at a different angle to the apertures in an adjacent radial arrays. FIG. 6 is a perspective view of a preferred arrangement of the detection apparatus of FIG. 4 showing the dome as a half sphere with LEDs in concentric circles in each of the nominal light locations. Each LED in each circle is equidistant and spaced by 10 degrees. Accordingly, there are 6 LEDs on the first circle, 12 on the second, 18 on the third, etc. Each LED points towards the focal point of the sphere which, in this embodiment is 480 mm from the interior surface of the sphere. Each LED is capable of emitting 100-120 lm. The number of circles is between 7 and 9 with the number of LEDs in each circle calculated using the formula:

Number of Circle (Number of Circle+1)/2*6

Each LED may be individually selected or it is possible to light multiple LEDs simultaneously.

In an alternative embodiment the concave support structure 10 is not provided with apertures but instead the lights are located directly to the concave support. In a particularly elegant version of this the lights are provided as a mat 22 mounted array of separately electable LED lights. The mat may be preformed and tested prior to assembly onto the concave surface with 1000 or more individual LEDs which can be mounted at relative spacing to each other. The greater the number of individual lights the more accurate the detection of the high angle boundary. For large numbers of individual lights it is possible to detect boundaries on a single crystal article that have very similar, but different, angles.

Advantageously, the arrangement of LEDs permits rapid indexing between the nominal light locations which, when sequenced with the detector enables quick and accurate location of the angle boundary between crystal grains. LEDs are robust and there are no moving parts.

The pre-provided lights also allow multiple LEDs to be lit simultaneously to bathe the illuminated article in a uniform background light.

Figure 7:
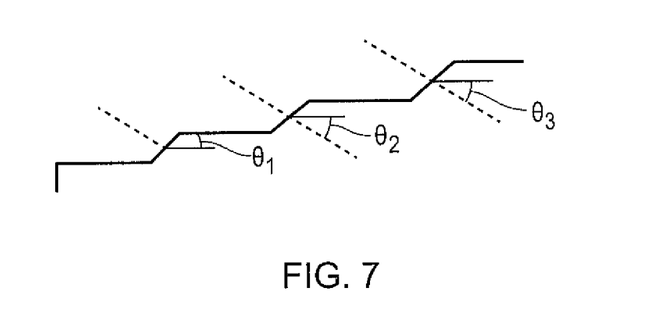
FIG. 7 depicts an alternative arrangement of the apparatus for detecting a high angle boundary.

Although the illumination support has been shown to be curved, in practice it is easier to manufacture as a faceted component as depicted in FIG. 7. Advantageously, such a support can be cheaply manufactured from polystyrene. The support has a series of parallel faces which are interleaved with angled surfaces, the angles of which are perpendicular to the angles $\theta_1$, $\theta_2$, $\theta_3$ of the respective apertures extending from the angled surface to the rear of the illumination support. The angles $\theta_1$, $\theta_2$, $\theta_3$ are selected to intersect at the surface of the article to be examined. The difference between the angles $\theta_1$, $\theta_2$, $\theta_3$ is the same as the angle a shown in FIG. 4. A difference of 10 degrees has been found to be sufficient.

The apertures are sized to receive a pen, lipstick, or other light that provides a narrow beam of light. To avoid reflection of light off the internal walls of the aperture the outlet of the light source is aligned with the outlet of the aperture at the convex surface of the illumination support.

Each nominal light location may be provided with a respective light or, more frequently, a single light is provided that is removable from a first nominal light location and moved to a further nominal light location. The determination of the location of the further nominal light location may either be based on a predetermined sequential series i.e. 16a, 16b, 16c . . . 16n, 18d, etc. or based on a calculation within the processor which takes into account the image detected from the first nominal light location and/or movement of the part relative to the detector. This approach is more efficient than the sequential approach, particularly where there are many nominal light locations, as it is possible to quickly determine which nominal light location is likely to indicate the high angle boundary.

Figure 8:
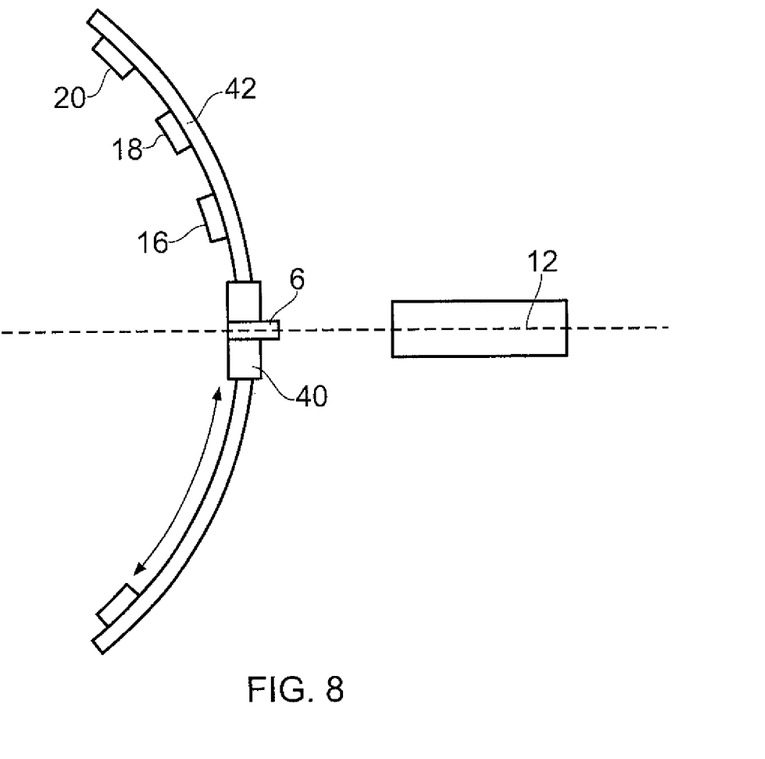
FIGS. 8 and 9 depict alternative views of an alternative embodiment of an apparatus for detecting a high angle boundary.
Figure 9:
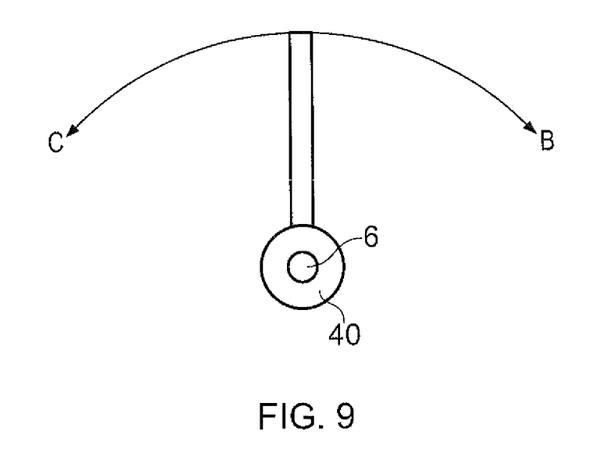

In a further embodiment which is shown in FIG. 8 and FIG. 9 the nominal light locations are provided on a curved arm 42 that is mounted through a bearing to the detector 6 to enable the arm to sweep 360 degrees around the detector in either direction or C. The nominal light locations 16, 18, 20 may be provided by a single light that traverses along the arm as shown below the axis line or by a plurality of lights spaced apart along the arm at regular intervals as shown above the axis line. It will be appreciated that the traversable light coupled with the sweepable arm permits a large number of selected light location. The curve of the arm may be selected such that the traversable light or plurality of lights are inherently directed to the focal point of the detector. Alternatively, each light may be mounted to a gimbal or other device which permits it to be directed to the focal point. It will be appreciated that multiple arms may be provided, preferably at fixed orientation to each other, to reduce the angular sweep required in either direction B or C to cover the whole 360 degrees for inspection.

In each of the above embodiments the detector may be capable of capturing static or moving images in digital or analogue form. It is preferred, however, that the detector is a digital camera that captures still images.

The operation of the device will now be described with reference to a single crystal turbine blade which is loaded onto a carrier to present a surface to a digital still image camera 6. The camera is connected to a processing unit 12 that has the capability of instructing the camera to capture a digital image of the surface. The carrier 30 can rotate and translate the blade 8 through 5 axis and preferably can present multiple surfaces of the blade to the camera.

Single crystal nickel alloys advantageously have a generally cubic grain structure. The advantage will be described in more detail later in the specification. The primary grain of the turbine blade is measured by locating the blade onto the carrier and presenting it to the camera and the light. The root of the blade faces towards the camera and illuminated by the light.

The processor selects a light location from the nominal light locations and light is emitted onto the article from the selected light location. The light may be permanently in place at the selected light location or may have to be moved to the selected light location. The light is used to illuminate the article and an image of the article captured by the camera.

A further light location is selected from the nominal light locations and the article illuminated from the further light location and an image of the article captured. Prior to the image capture the article is manoeuvred to maintain a light/surface/camera triangle which reflects light from the surface to camera. The position of the further light location is selected either by following a predetermined sequence or from the processing unit that has analysed a preceding image. The process repeats using as many further light locations as deemed necessary to provide an image of the blade that identifies a high angle boundary between crystals, if one is present.

The detection process preferably runs through three routines entitled: course, fine and superfine. The main difference between the three routines being the tilt step and circumferential rotation step. Initially the part is loaded such that the surface is brought into a position where the primary grain reflects such that a contrast with the secondary grain can be seen. Where possible this surface is brought into approximate perpendicularity with the optical axis. A first course spiral is executed where the component is run through a tilt and rotation program where the tilt of the part is increased in 5 degree intervals and an image is taken every 40 degrees as the part is rotated about the axis. The light is kept in the same position throughout the sequence. The tilt increases from 0 degrees to 20 degrees but if the most intense point is not in the final circle the tilt is increased further.

The graphical representation of the captured data will indicate two points of maximum intensity with the first representing the primary grain and the second representing the secondary grain. For each of the grains the maximum points are selected and a spiral of a tilt increasing by 2 degrees and an image taken every 30 degrees for a fine scan which indicates the maximum point with greater accuracy. The same process is repeated using the maximum points for the primary and secondary grains in a super fine scam with to tilt increasing by 0.5 degrees and an image is taken every 40 degrees as the part is rotated about the axis.

Once the maximum intensity is found for both the primary and secondary grains it is possible to calculate the reflectivity index using a transformation matrix for each position. The transformation for each position is:

$${}^{UF}_{G}T$$

Where, G is the reference frame for the grain and the two vectors that represent the grain direction relative to G can be computed using the equation:

$${}^{G}V_{NX1} = ({}^{UF}_{G}T)^{-1} \times {}^{UF}V_{NX1}$$

and $${}^{G}V_{NX2} = ({}^{UF}_{G}T)^{-1} \times {}^{UF}V_{NX2}$$

Where $${}^{UF}V_{NX} = \frac{{}^{UF}V_{LK} + {}^{UF}V_{CAM}}{2}$$

The angle between the two vectors is the grain reflectivity value $$\theta = \frac{V_{NX1} \times V_{NX2}}{\|V_{NX1}\|\|V_{NX2}\|}$$

Rather than using the exact peak position, particularly where the captured intensity is close to a neighbours, it can be beneficial to use a weighted average of all the vectors that have 90% or more of the peak value.

The calculated reflectivity index has been found to correlates well with current x-ray techniques and it will be appreciated that the invention offers a number of advantages. The support with the nominal light locations provides a repeatable apparatus for accurately identifying high angle boundaries, should one be present, within a turbine blade. The camera, which may be the heaviest and most expensive component of the apparatus is held in a fixed location. Where multiple lights are used, one in each of the nominal light locations, it is possible to quickly index between locations in sequence with the image capture to enable fast identification of a high angle boundary, if present.

Although the present invention has been described with respect to identification of high angle boundaries in single crystal articles such as turbine blades the invention may also be used to detect other artefacts in other components, for example inclusions, plus metal.

The invention claimed is:

1. A method of determining the value of a boundary between a primary grain and a secondary grain in a component, the method comprising the steps of:
    identifying a boundary between a primary grain and a secondary grain which are presented on a surface of the component;
    illuminating the primary grain with a beam from a light source and manipulating the relative orientation of the surface, beam and a detector detecting the light reflected from the surface and determining a first relative orientation which provides the peak reflectance of the beam to the detector;
    illuminating the secondary grain with a beam from a light source and manipulating the relative orientation of the surface, beam and the detector detecting the light reflected from the surface and determining a second relative orientation which provides the peak reflectance of the beam to the detector; wherein the difference between the first and second relative orientations gives a value that indicates the magnitude of the angle boundary.

2. A method according to claim 1, wherein the value is compared to a threshold range having high, low and medium tolerance ranges, the method including a step of sentencing the component dependant on the band in which the value corresponds.

3. A method according to claim 2, wherein the component is scrapped when the value corresponds to the high tolerance range.

4. A method according to claim 2, wherein the component is passed as fit for service when the value corresponds to the low tolerance range.

5. A method according to claim 2, wherein the component is passed for further analysis when the value corresponds to the medium tolerance range.

6. A method according to claim 5, wherein the further analysis inspects the surface with an x-ray to determine the value of the boundary.

7. A method according to claim 1, wherein the step of manipulating the surface includes adjusting the roll, pitch and/or yaw of the surface.

8. A method according to claim 7, wherein the roll, pitch and yaw are adjusted by moving the surface in a first ellipse or circle about a pivot point.

9. A method according to claim 8, wherein reflectance values are taken at a plurality of locations as the surface is moved in the circle or ellipse about the pivot point.

10. A method according to claim 8, wherein the surface is moved in a further ellipse or circle of different size to the first ellipse or circle.

11. A method according to claim 1, wherein the relative orientation is an average of the relative orientations giving a reflectance value that is within 10 percent of an absolute peak reflectance.

* * * * *